(12) United States Patent  (10) Patent No.: US 6,685,538 B1
Farre                     (45) Date of Patent:    Feb. 3, 2004

(54) MACHINE FOR MACHINING A VOLUME, IN PARTICULAR AN INLAY, BY AUTOMATIC DUPLICATING

(76) Inventor: Pierre Farre, 83 Bis Rue Des 36 Ponts, F-31400 Toulouse (FR)

( * ) Notice: Subject to any disclaimer, the term of this patent is extended or adjusted under 35 U.S.C. 154(b) by 0 days.

(21) Appl. No.: 09/868,318

(22) PCT Filed: Dec. 17, 1999

(86) PCT No.: PCT/FR99/03168
§ 371 (c)(1),
(2), (4) Date: Aug. 14, 2001

(87) PCT Pub. No.: WO00/36992
PCT Pub. Date: Jun. 29, 2000

(30) Foreign Application Priority Data

Dec. 18, 1998 (FR) .............................. 98 15984

(51) Int. Cl.[7] .............................................. B24B 49/00
(52) U.S. Cl. ................................. 451/8; 451/9; 451/29; 451/281; 433/51; 433/52
(58) Field of Search ........................ 451/8, 9, 29, 31, 451/281; 433/51, 52, 25, 76

(56) References Cited

U.S. PATENT DOCUMENTS 4,766,704 A  *  8/1988  Brandestini et al.
5,256,011 A  * 10/1993  Taylor
5,383,752 A  *  1/1995  Rheinberger et al. ........ 409/105
5,993,123 A  * 11/1999  Allred, III et al.
6,095,726 A  *  8/2000  Scott et al.

* cited by examiner

*Primary Examiner*—Lee D. Wilson
(74) *Attorney, Agent, or Firm*—Dykema Gossett PLLC

(57) ABSTRACT

A machine for machining a volume, in particular an inlay, by automatic duplicating, includes an abrasive disc having a rotatable drive, a support for a blank of the volume, the disc and the blank being rotatable, a rotatable duplicator support a touch-sensing probe capable of being urged into contact with the duplicator outer surface, there being relative displacement between the blank support and the disc and between the duplicator support and the touch-sensing probe so as to enable the disc and the touch-sensing probe to remain permanently in contact with the blank and the duplicator, and a mobile carriage having at least two degrees of freedom on which are mounted the support for the blank and for the duplicator, the carriage commanding and controlling the drive of the rotatable disc and the duplicator support.

19 Claims, 3 Drawing Sheets

MACHINE FOR MACHINING A VOLUME, IN PARTICULAR AN INLAY, BY AUTOMATIC DUPLICATING

BACKGROUND OF THE INVENTION

The present invention relates to the field of machines that allow a machining by the removal of material by reproducing a model, more particularly applied to the medical field, particularly the dental field, for manufacturing ceramic components intended to replace all or part of a dental crown, and relating in particular to machines comprising a machining tool with an axis of symmetry and having at least one degree of freedom in rotation about said axis of symmetry, means for driving the rotation of the said machining tool about its axis of symmetry, means of securing a blank, in which said volume is machined, having at least one degree of freedom in rotation, means for driving the rotation of said blank-securing means, means for securing a template, having at least one degree of freedom in rotation, means for driving the rotation of said template-securing means, a feeler capable of coming into contact with the exterior surface of said template, means for bringing about relative movement between said blank-securing means and said machining tool, on the one hand, and between said template-securing means and said feeler on the other hand, said movement means allowing the machining tool and the feeler to remain in constant contact with, respectively, said blank and said template.

A known method and to an apparatus for manufacturing volumes by copying in. dentistry, particularly for inlays, is disclosed in U.S. Pat. No. 5,135,393. The machine is an eight-axis machine in which all movements of the moving parts of the machine are performed manually by the operator, except for the rotating of the tool which is done by a motor. More specifically, the machine comprises a first carriage carrying a feeler and a tool support which are held together, the axes of which are mutually parallel and are perpendicular to an axis of movement and translation of the feeler and of the tool support; furthermore, this first carriage is free to rotate and to translate along axes respectively parallel and perpendicular to the axis of translation of the feeler and of the tool joined together; this first carriage is kept pressing and moved by an operator during machining against a second free-rotation carriage which carries the template and the blank themselves which are free to rotate on this second carriage; so that under the pressure and movements brought-about by the operator, the feeler travels over the surface of the template and the tool machines the blank accordingly; the template and the blank are incidentally linked in rotation so that when the operator with one hand turns the template, the blank follows this rotational movement, whereas with the other hand the operator takes care to cause the feeler to travel over the surface of the template. A machine such as this is complicated and expensive because of the high number of degrees of freedom and is tricky to use because the copying precision depends on the quality of service provided by the operator.

The prior art in particular teaches a machine of this type with document WO 96/05 782, comprising a diamond-tipped machine tool actuated by a high-speed turbine, a feeler placed on the same machine body of the tool, the tool and the feeler being able to move in translation and in rotation so as to follow the profile of a model secured in alignment with the blank, such a machine allowing a model to be reproduced precisely but entailing a mechanism which is cumbersome, bulky and expensive, particularly because of the high speeds at which the tool rotates. Furthermore, the small-diameter tool which allows small details to be reproduced, which rotates at high speed, may wear rapidly and therefore cause the machine to be expensive to use.

SUMMARY OF THE INVENTION

The present invention essentially sets out to alleviate these drawbacks and to provide other advantages. More specifically, it consists in a machine for machining at least one volume, particularly an inlay, automatically by copying, comprising at least:

a machining tool with an axis of symmetry and having at least one degree of freedom in rotation about said axis of symmetry, means for driving the rotation of the said machining tool about its axis of symmetry, means for securing a blank, in which said volume is machined, having at least one degree of freedom in rotation, means for driving the rotation of said blank-securing means, means for securing a template, having at least one degree of freedom in rotation, means for driving the rotation of said template-securing means, a feeler capable of coming into contact with the exterior surface of said template, means for bringing about relative movement between said blank-securing means and said machining tool, on the one hand, and between said template-securing means and said feeler on the other hand, said movement means allowing the machining tool and the feeler to remain in constant contact with, respectively, said blank and said template, means for commanding and controlling said means for driving the rotation of the machining tool, said means for driving rotation of the template-securing means and said movement means, said machine being characterized in that said machining tool is an abrasive disk and in that said movement means comprise a moving carriage on which said blank-securing means and said template-securing means are mounted so that they are free to rotate, said moving carriage having at least two degrees of freedom of movement.

The abrasive disk which makes it possible to reduce the rotational speed of the machining tool appreciably, and the arrangement of the movement means which allow the blank and the template to be moved rather than the machining tool, lead to a significant reduction in the weight and cost of the machine.

According to an advantageous characteristic, said two degrees of freedom of said moving carriage are one degree of freedom in rotation and one degree of freedom in translation, and said movement means comprise means for driving the translation and means for driving the rotation of said moving carriage.

According to an advantageous characteristic of the foregoing, the machine according to the invention comprises a rigid support, and said means for driving the translation of said moving carriage comprise a first motor connected completely to said rigid support, in that said means for driving the rotation of said blank-securing means and said means for securing the template comprise a second motor connected to said first motor via a screw-nut connection, and said moving carriage is free in rotation about the output shaft of said second motor, said output shaft being guided in rotation and in translation by said rigid support.

According to an advantageous characteristic of the foregoing, said means for driving the rotation of said moving carriage about the output shaft of said second motor comprise the friction forces generated by the rotation of said blank-securing means and of said means of securing the template.

According to an advantageous characteristic of the foregoing, said blank-securing means and said means for securing the template are connected completely and have aligned axes of rotation.

According to an advantageous characteristic of the foregoing, the axis of rotation of said abrasive disk is parallel to the axes of rotation of said blank-securing means and of said means for securing the template, said rigid support having a flat wall perpendicular to said axis of rotation of the abrasive disk separating a machining compartment from a drive compartment.

According to an advantageous characteristic of the foregoing, the axis of rotation of said abrasive disk and the output shaft of said second motor are mounted in identical respective bearing supports.

The flat wall perpendicular to the axes of rotation makes the bearing supports easier to mount and the use of identical bearing supports lowers manufacturing costs.

According to an advantageous characteristic, said feeler is secured rigidly to said rigid support so as, by its abrasion resulting from the rubbing against the template, to compensate for the wear of said abrasive disk, thus making the precision of the reproduction independent of tool wear.

According to another advantageous characteristic, the machine according to the invention comprises means of moving said feeler radially, making it possible to establish a given dimensional ratio at which the inlay is reproduced with respect to the template, in a plane perpendicular to an axis of rotation of said template.

This characteristic allows the radial reproduction ratio to be varied without varying the axial reproduction ratio, used particularly the case of the manufacture of inlays, so as to form a cementing space or so as to compensate for errors which may impair the fit, without this detracting from the longitudinal dimension.

According to another advantageous characteristic, said feeler has a thickness greater than the thickness of said abrasive disk so as to increase the longitudinal dimension of the inlay with respect to that of said template.

Aside from compensating for errors in flatness or due to the vibrations of the disk, this characteristic allows compensation for the removal of material carried out when the finished part is polished.

According to another advantageous characteristic, said blank-securing means and said means for securing the template are connected by a screw-nut connection, said blank-securing means being secured rigidly to one of said elements—screw or nut—and said template-securing means being secured rigidly to the complementary other one of said elements—nut or screw.

This characteristic allows a more ergonomic machine according to the invention, the blank-securing means being fastened to the template-securing means by a screw-nut connection. Thus, the operator can easily, with two hands, assemble the blank and the template, each held in a respective hand, and, through the reverse movement, disassemble the part obtained from the template, and do so without immobilizing the axis of rotation thereof. This characteristic also makes it possible to eliminate any play there might be between the blank and the template.

According to another advantageous characteristic, the machine according to the invention comprises means for automatically stopping operation at the end of machining by detecting that said moving carriage is in a given position. At the end of machining, as the feeler no longer holds the template, the moving carriage moves toward the axis of symmetry of the abrasive disk, it being possible for the automatic stop means to be advantageously actuated during this movement.

According to another advantageous characteristic, the machine according to the invention comprises a disk which is abrasive over all or part of its two opposite faces, said two opposite faces converging toward the periphery of the disk. As the disk essentially works on a face in opposition to the movement of the moving carriage, turning over the disk, one face of which is worn, makes it possible to double the life of this disk.

According to another advantageous characteristic, the machine according to the invention comprises means for slaving said movement means to the force exerted by the abrasive disk on the blank. A characteristic such as this makes it possible to optimize the machining time.

According to another advantageous characteristic, the machine according to the invention comprises means of lubricating said machining disk by splash lubrication. This characteristic makes it possible to avoid the use of a machining lubrication circulation pump.

According to another advantageous characteristic, the machine according to the invention comprises means for reversing the direction of rotation of said abrasive disk. It is therefore possible to use the two opposite sides of the abrasive grains of a disk, thus optimizing the cost of using the machine.

According to another advantageous characteristic, the machine according to the invention comprises means for automatically clearing said moving carriage at the end of machining. This makes it possible to achieve better ergonomics, automatically clearing the carriage at the end of machining allowing easier access for disassembling the machined part and the template.

According to another advantageous characteristic, the machine according to the invention comprises a centering jig allowing the blank to be secured to said blank-securing means, and allowing the template to be secured to said template-securing means in such a way that the inlay to be obtained lies within the volume of the blank. This characteristic makes it possible to avoid the volume which is to be machined being positioned with respect to the template in such a way that the volume would lack material with respect to this template.

According to another advantageous characteristic, said blank and said template are secured to their respective securing means via at least one of their respective ends.

Other characteristics and advantages will become apparent upon reading the description which follows of one exemplary embodiment of a machine according to the invention, accompanied by the appended drawings, the example being given by way of illustration and without any restrictive interpretation of the invention being derivable therefrom.

DETAILED DESCRIPTION OF THE INVENTION

Figure 1:
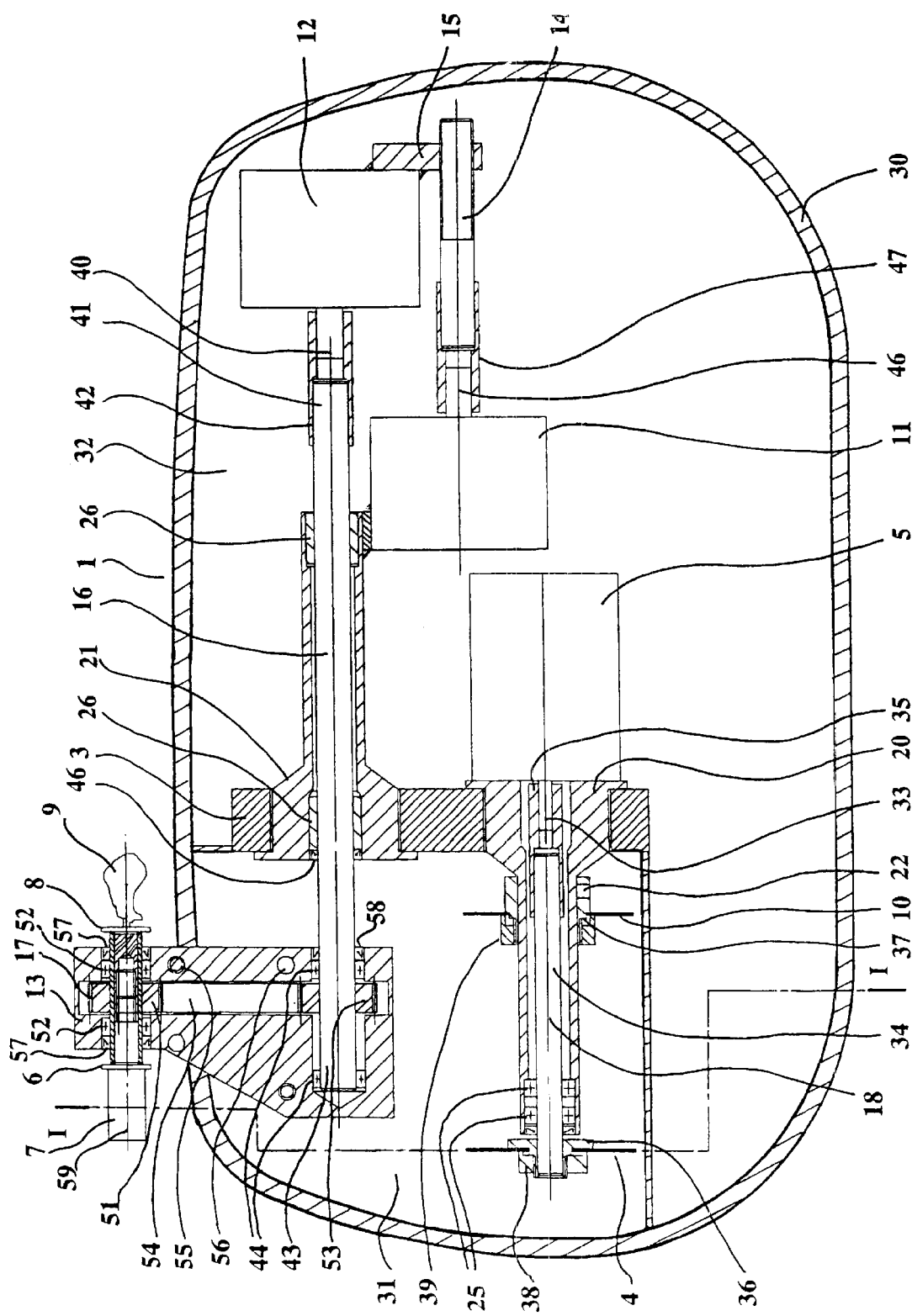
FIG. 1 depicts a schematic partial view from above in section on the line II—II of FIG. 2, of one exemplary embodiment of a machine according to the invention, making it possible to machine at least one volume, particularly an inlay, automatically by copying.

The machine 1 depicted in FIG. 1, for machining at least one volume, particularly an inlay; automatically by copying, comprises an abrasive disk 4 with an axis of symmetry 18 and having at least one degree of freedom in rotation about the axis of symmetry 18, means 5 for driving the rotation of the abrasive disk 4 about its axis of symmetry, means 6 for securing a blank 7 in which the volume is machined and having at least one degree of freedom in rotation, means 12, 16, 17 for driving the rotation of the blank-securing means 6, means 8 for securing a template 9 having at least one degree of freedom in rotation, the means 12, 16, 17 also driving the rotation of the template-securing means 8, a feeler 10 designed to come into contact with the exterior surface of the template, means 11, 13, 14, 15, 16 of relative movement between the blank-securing means 6 and the abrasive disk 4, on the one hand, and between the template-securing means 8 and the feeler 10 on the other hand, the movement means allowing the abrasive disk 4 and the feeler 10 to remain in constant contact with, respectively, the blank and the template, means for commanding and controlling the means 5 for driving the rotation of the abrasive disk 4, and the means 12 also driving the rotation of the means for securing the template 9 and the movement means 11.

The movement means comprise a moving carriage 13 on which the means 6 for securing the blank 7 and the means 8 for securing the template 9 are mounted so that they can rotate freely, the moving carriage 13 advantageously having two degrees of freedom of movement, namely one degree of freedom in rotation and one degree of freedom in translation. The movement means further comprise means 11, 14, 15 for driving the translation and means for driving the rotation of the moving carriage 13.

The machine depicted in FIG. 1 further comprises a rigid support 3. The means for driving the translation of the moving carriage 13 comprise a first motor 11 connected completely to the rigid support 13. The means for driving the rotation of the means 6 for securing the blank 7 and of the means 8 for securing the template 9 comprise a second motor 12 connected to the first motor 11 via a screw-nut connection 14 and 15, the moving carriage 13 being free to rotate about the output shaft 16 of the second motor, the output shaft 16 being guided in rotation and in translation via a bearing support 21 rigidly secured to the rigid support 3 as depicted in FIG. 1 and explained in detail later on.

The axis of rotation 18 of the abrasive disk 4 is parallel to the axes of rotation of the means 6 for securing the blank 7 and of the means 8 for securing the template 9, the rigid support 3 advantageously adopting the form of a flat wall perpendicular to the axis of rotation 18 of the abrasive disk 4, thus dividing a machining compartment 31 from a drive compartment 32. The axis of rotation 18 of the abrasive disk 4 is mounted in a bearing support 20, advantageously identical to the bearing support 21, guiding the output shaft 16 of the second motor 12, as depicted in FIG. 1. The fact that the bearing supports 20 and 21 are identical gives the machine according to the invention a simplicity of design and reduces the costs of manufacture.

Figure 2:
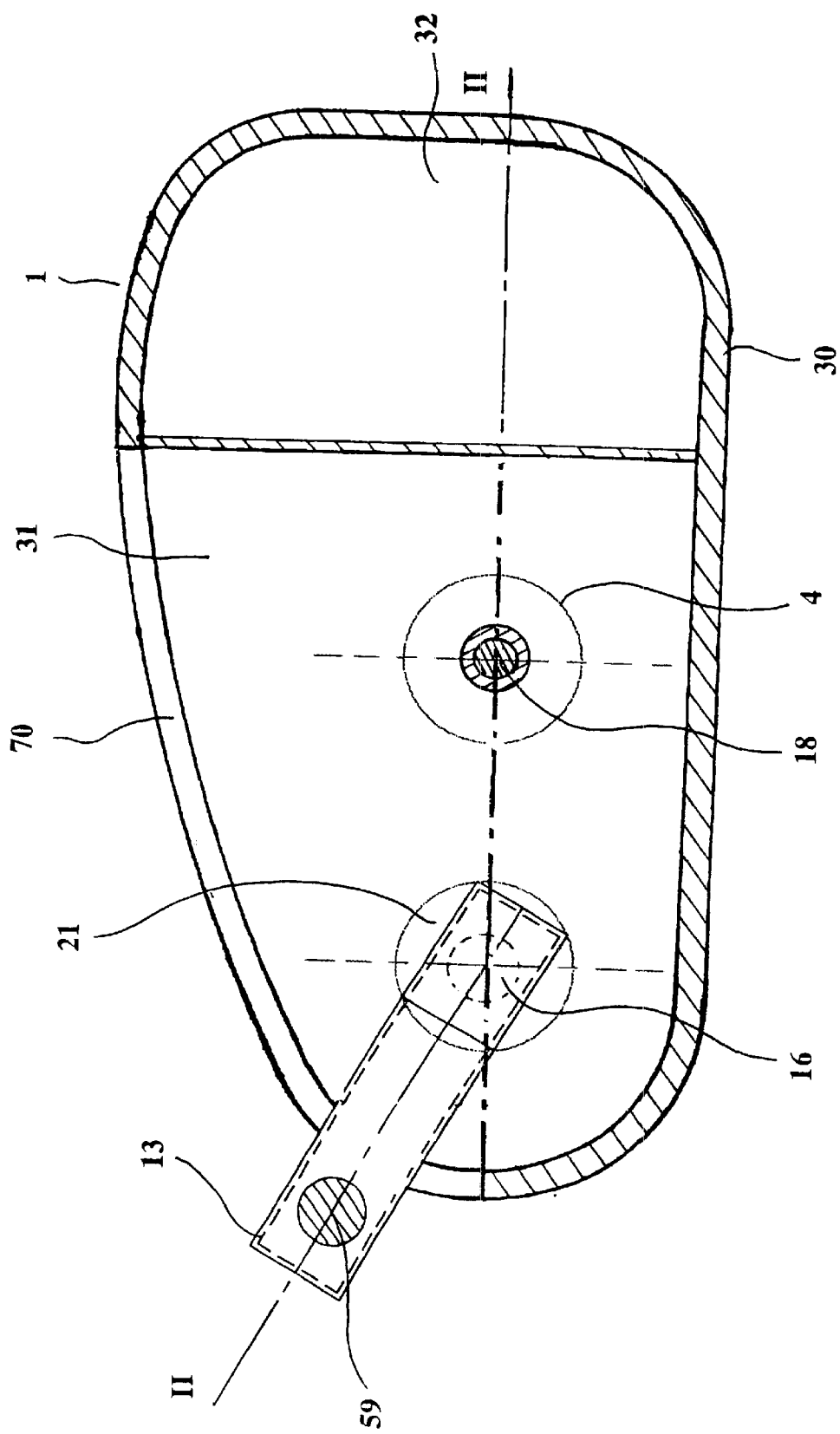
FIG. 2 depicts a view in cross section on the line I—I of FIG. 1.

All of the means that make up the machine according to the invention are advantageously housed in an enveloping casing 30 which protects these constituent means, acts as a container for a machining lubricating fluid, as will be expanded upon later on, and improves the appearance of the machine, as depicted in FIGS. 1 and 2. The rigid support 3 will preferably adopt the form of a flat wall capable rigidly of supporting, on the one hand, the bearing support 20 on which are advantageously mounted, free to rotate, the shaft 34 of the abrasive disk 4, rigidly, the support 22 of the feeler 10 and the drive motor 50 and, on the other hand, the bearing support 21 on which are advantageously rigidly mounted the motor 11, and, free to rotate and to translate, the output shaft 16.

The output shaft 33 of the drive motor 5 is coupled in rotation in any known way, fir example via a coupling sleeve 35, to a shaft 34 on which the abrasive disk 4 is centered and secured, as depicted in FIG. 1. The shaft 34 is guided in rotation in the bearing support 20 in any appropriate way depending on the rotational speed of the disk, via ball- or needle-bearings 25, for example, in the case of a disk rotating at a speed of the order of 250 revolutions per second approximately. A sealing ring will be placed around the shaft 34, as depicted in FIG. 1, so as to hold the lubricant in the machining compartment 31. The abrasive disk 4 will be secured removably to the shaft 34, for example via a chuck 36 with a central nut 38, so that it can be changed, and may advantageously be mounted reversibly for the preferred case in which the disk is abrasive on all or part of its two opposite faces, so as to allow the disk to be turned over. The abrasive disk will preferably be a diamond tipped disk, the two opposite faces of which converge toward the periphery of the disk, a cross section along a radius of the disk preferably forming an isosceles triangle, the tip of which consists of the periphery of the disk.

The feeler 10 is advantageously rigidly secured to the rigid support 3, more specifically to the bearing support 20, itself connected completely and rigidly to the support 3, as depicted in FIG. 1. Mounting the feeler 10; so that it is fixed, makes it possible, through its abrasion resulting from the friction against the rotating template 9, to compensate for the wear of the abrasive disk 4. As depicted in FIG. 1 for example, the feeler 10 connected to a sleeve 22 is sandwiched in a screw-nut connection 39, the sleeve 22 being secured rigidly and so that it is adjustable in terms of rotation about the bearing support 21 by virtue of a central bore. A radial set screw (not depicted) may, for example, be used to immobilize the sleeve in the bearing support 20.

The machine depicted in FIG. 1 advantageously comprises means for moving the feeler 10 radially, making it possible to establish a given dimensional ratio with which the inlay is reproduced with respect to the template 9, in a plane perpendicular to an axis of rotation of the template. The radial movement means advantageously consist of a shoulder 37 formed on the sleeve 22 and off-centered with respect to the bore for centering the latter on the bearing support 20. Thus, rotating the sleeve 22 about the bearing support 20 allows the feeler 10 to be moved radially by virtue of the eccentricity of the shoulder 37.

If the feeler 10 is fixed, the latter may adopt the form of a sector of a disk, the peripheral part of which reproduces part of the periphery of the abrasive disk 4.

The machine may advantageously comprise a means for axially moving the sleeve 22, thus possibly allowing the machining of shorter blanks. This means of axial movement may, for example, consist of an intermediate ring (not depicted) between the sleeve 22 and the bearing support 20; the intermediate ring will be free to translate on the bearing support, and the sleeve 22 free to rotate on the intermediate ring, or vice-versa.

Advantageously, the feeler 10 has a thickness greater than the thickness of the abrasive disk 4 so as to increase the longitudinal dimension of the part to be obtained, for example an inlay, compared with that of the template 9, and also so as to compensate for errors in flatness or errors due to the vibrations of the disk. The increase in the longitudinal dimension of the copy makes it possible to compensate for the removal of material due to the polishing that the part needs after it has been machined on the machine according to the invention.

The output shaft 16 is connected in rotation-at a first 41 of its ends to the rotational drive shaft 40 of the second motor 12 possibly via a coupling sleeve 42, and is connected in translation but free in terms of rotation at its second end 43 to the moving carriage 13, preferably via rolling bearings 44, for example ball bearings, needle bearings or the like, as depicted in FIG. 1. The output shaft 16 is guided in rotation and in translation in the bearing support 21, preferably by virtue of plain bearings 26. A sealing ring 46 is fitted around the shaft 16 so as to seal the drive compartment 32 from the lubricant found in the machining compartment 31.

The body of the first motor 11 is secured rigidly to the bearing support 21, and its rotational drive shaft 46 is connected in rotation to the screw 14 possibly via a coupling sleeve 47. The screw 14 is engaged in a nut 15 connected in rotation and in translation to the body of the second motor 12, as depicted in FIG. 1, so that rotation of the drive shaft 46 of the first motor 11 leads to a translation movement of the body of the second motor 12 without causing the latter to rotate, causing a translational movement of the shaft 16 carrying the moving carriage 13.

The first motor 11 is preferably a stepping motor making it possible to cause a translational movement of the shaft 16 of the order of 1 to 2 mm per minute; the second motor 12 is preferably a stepping motor making it possible to cause a rotation of the shaft 16 of the order of one revolution per second; the abrasive disk drive motor 5 must allow the disk to rotate at a speed of the order of 250 revolutions per second.

The moving carriage 13 is in the form of an arm, with the output shaft 16 connected to its first end as described previously, and with the blank-securing means 6 and said means 8 for securing the template 9 mounted so that they can rotate freely at its second end, as depicted in FIG. 1. Placed inside the carriage is a transmission for transmitting the rotational movement of the output shaft 16 to the blank-securing and template-securing means, for example a belt drive 17 as depicted in FIG. 1.

Figure 3:
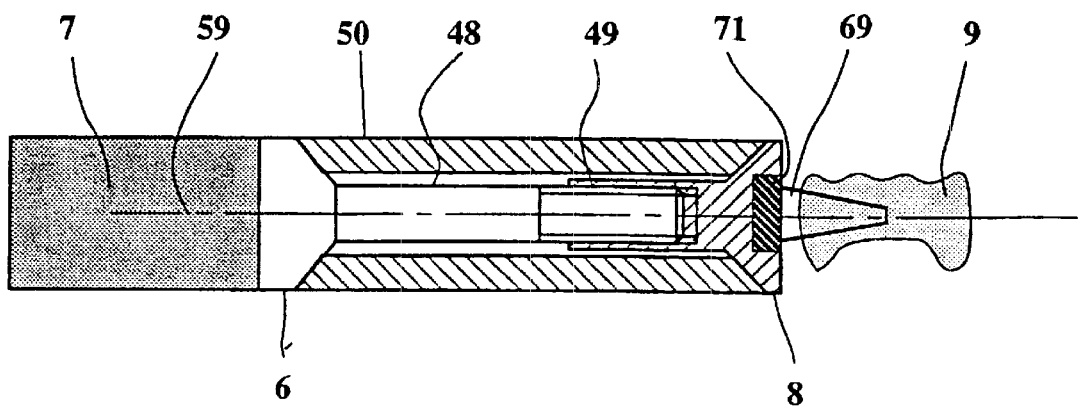
FIG. 3 depicts an enlarged first detail of the machine according to FIG. 1.

The means 6 for securing the blank 7 and the means 8 for securing the template 9 are advantageously connected completely and have axes of rotation which are aligned, forming a single axis 59, by a removable link exerting a mutual pull of one toward the other, preferably a screw-nut connection 48, 49 as depicted more particularly in FIG. 3. The means 6 for securing the blank 7 are secured to one of the elements—screw 48 or nut 49—of the screw-nut connection, and the means 8 for securing the template 9 are secured to the complementary other one of the element—nut or screw—of the screw-nut connection. The means 8 for securing the template 9 may consist of a head of the nut 49 and the means 6 for securing the blank 7 may consist of the head of the screw 48, as depicted in FIG. 3.

A tubular element 50 will advantageously be sandwiched between the screw 48 and the nut 49, thus, via bearing surfaces which are preferably conical at its ends, aligning the blank-securing means 6 and the template-securing means 8. The tubular element 50 is secured to a wheel 51 which takes the rotational drive belt 17, as depicted in FIG. 1. The output shaft 16 is secured to a wheel 53 with which the belt 17 engages to transmit the rotational movement of the tubular element 50. As depicted in FIG. 1, the belt drive 51, 53, 17 is preferably mounted inside the moving carriage 13 where the housing 54 is produced for this purpose. In order to access the housing 54, the moving carriage may adopt a structure in two parts assembled and positioned one on the other removably by means of screws 55 and pegs 56 respectively, for example. The wheels 53 and 51 will preferably be placed between the two bearings 44 supporting the output shaft 16 and the two bearings 52 supporting the tubular element 50, respectively. As depicted in FIG. 1, sealing rings 57, 58 will be mounted around the tubular element 50 and the output shaft 16 so as to protect the belt drive and the bearings placed inside the moving carriage 13 from the lubricating fluid placed in the machining compartment 31.

The screw-nut mounting 48–49 allows the user, having secured the blank and the template on the head of the screw and the head of the nut respectively, as will be explained later on, to mount these elements on the machine, each in one hand, in an operation of screwing through the tubular element 50. By virtue of the screw-nut connection 48, 49 in collaboration with the conical bearing surfaces described above, the blank support and template support are mounted without play and are correctly aligned on one and the same axis of rotation. The tubular element 50 is mounted so that it can rotate freely on the carriage 13 via two bearings, preferably rolling bearings 52, as depicted in FIG. 1.

The machine according to the invention advantageously comprises in full or part of itself, a centering jig 60 which allows the blank 7 to be secured to the blank-securing means 6 and allows the template 9 to be secured to the template-securing means 8 in such a way that the part to be obtained, particularly the inlay, is inscribed inside the initial volume of the blank.

Figure 4:
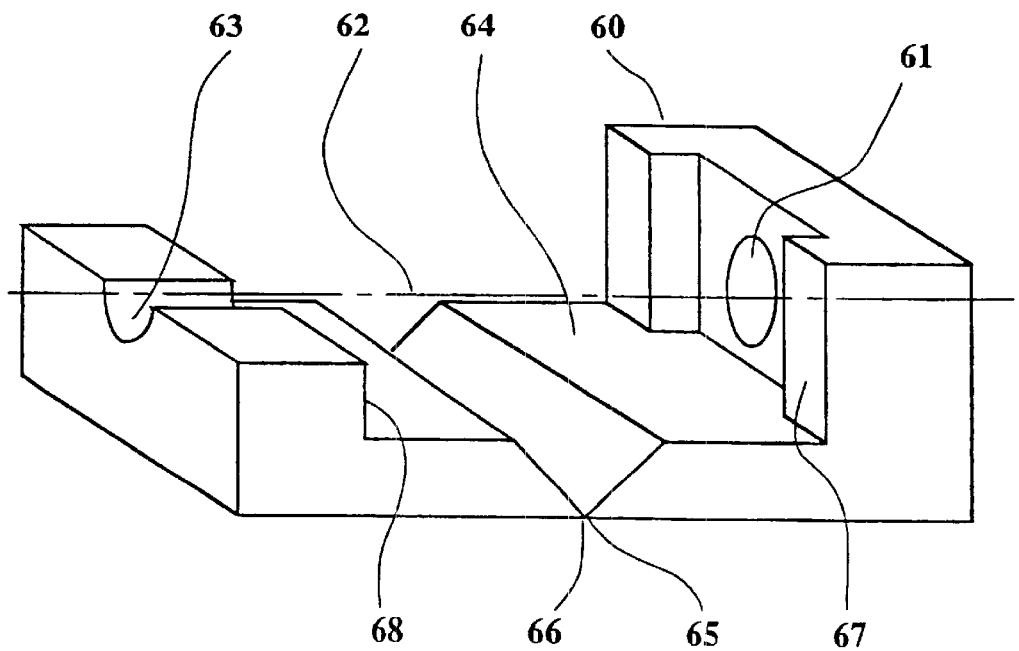
FIG. 4 depicts an exemplary embodiment of a centering jig for the machine according to FIG. 1.

One exemplary embodiment of such a jig is depicted in FIG. 4, enlarged and in perspective. The jig 60 comprises a housing 61, preferably tubular, which represents the exterior shape of the blank and which may be slightly smaller in order to compensate for positioning errors, the housing 61 defining an axis of symmetry 62, and a housing 63 similar to the housing 61 but open at the top and the axis of symmetry of which is colinear with the axis 62. Between the housings 61 and 63, the jig forms a clearance 64 that complements the exterior shape of the moving carriage 13 so that the latter can be inserted in it and positioned in such a way that the axis 62 of the jig is parallel to the axis of rotation 59 of the means for securing the blank 7 and means for securing the template 9. The jig 60 and/or moving carriage 13 will be equipped with any means allowing the operator easily to position the axes 62 and 59 parallel and keep them in this position with respect to one another for long enough to secure the blank and the template to their respective securing means. The exterior shapes of the jig 60 and of the moving carriage 13 will advantageously be used for this purpose to allow these to nest together in the desired position explained above. The flat walls 67 and 68 may be used to bear against the moving carriage.

To facilitate the operation that consists in nesting the jig 60 on the moving carriage 13, the jig may advantageously be equipped with a hinge means 65 allowing the clearance 64 to be opened up by folding the jig about an axis perpendicular to the axis 62, as depicted in FIG. 4. The hinge means will preferably be produced by a thinning 66 of a section perpendicular to the axis 62, altering the flexibility of a plastic material of which, in this case, the jig 60 is preferably made.

The tubular housing 61 of the jig will be of a shape that complements that of the blank covering the volume of the template used. It is thus understood that there may be as many jigs as there are essential shapes of templates possible according to the intended applications. The open housing 63 of the jig will be of a shape that complements that of the blank so as to allow the latter to be guided toward the corresponding securing means in a direction parallel to the tubular housing 61 and parallel to the axis 59.

The template 9 is first of all secured by one of its ends to its securing means 8, preferably by bonding, and preferably by distributing the material uniformly about the axis of rotation 59 of the securing means. The securing means 8 may comprise a spike 69 formed on the head of the nut 49, for example, which will penetrate a complementary housing in the template 9 in order to provide better securing, as depicted in FIG. 3. The spike 69 will be secured via an insulator 71 to the head of the nut 49. The means 8 for securing the template 9 with the associated template are then mounted on the machine 1 via the screw-nut connection 48, 49 as described earlier. Next, the jig 60 is fitted on the moving carriage 13 by inserting the template 9 in the tubular housing 61. The blank 7 is finally secured, preferably by bonding, by one of its ends to the corresponding securing means 6, in a position thus given by the jig 60 so that the volume of the template 9 is inscribed inside the volume of the blank 7.

The axis of rotation 59 of the blank 7 and of the template 9 is parallel to the axis of rotation 18 of the abrasive disk and the part of the feeler 10 in contact with the template 9 is aligned with the peripheral working part of the abrasive disk 4 along a straight line parallel to the axis 18 so as to obtain a copy which is identical to the template in a plane perpendicular to the axes 59 and 18.

When the motor 12 drives the rotation of the blank 7 and of the template 9 in a given direction, via the output shaft 16, the belt drive 17, 51, 53, the blank-securing means 6 and the means 8 for securing the template 9, the friction forces due to the rotational drive give rise to a torque which tends to cause the moving carriage 13 to rotate about the output shaft 16, and therefore to keep the template 9 and the blank 7 pressed respectively against the feeler 10 and against the abrasive disk 4. These friction forces may act in concert with the forces of gravity and/or the forces generated by the action of a spring (not depicted), as appropriate. If the motor 12 drives the blank 7 and the template 9 in the opposite direction of rotation to the previous one, it is necessary to use the forces of gravity and/or the forces generated by the action of a spring as explained hereinabove.

A The machine advantageously comprises means for reversing the direction of rotation of said abrasive disk 4, which can thus work in opposition or in a downstream direction depending on whether it is rotating in one direction or the other, this being in order to optimize the wear on the disk before it is replaced as a result of wear.

The means (not depicted) of command and control of the means for driving the rotation of the machining tool, of the means for driving the rotation of the means that secure the template and the blank, and of the movement means, comprise an electrical power supply, preferably a low-voltage DC supply arranged outside the casing 30 of the machine 1 and connected to the latter at the drive compartment 32 by a supply lead and an electric plug, both of which are sealed (not depicted), command and control electronics (not depicted) placed in the drive compartment 32, and software for the automatic control of at least a manufacturing cycle.

The machine depicted in FIG. 1 advantageously comprises means for automatically stopping operation at the end of machining by detecting that the moving carriage 13 is in the given position, for example when the feeler 10 is near to or on the axis 59 of rotation of the template.

The machine depicted in FIG. 1 furthermore advantageously comprises means for slaving the means for moving the moving carriage 13, more particularly the motor 11 that drives the translational replacement of the carriage, to the force exerted by the abrasive disks on the blank 7.

The machining compartment 31 will be filled up to a given level with a lubricating fluid, particularly water, so as to provide correct lubrication and correct cooling of the abrasive disk 4 by splash lubrication and will be sealed so that the fluid does not enter the drive compartment 32.

The machine depicted in FIG. 1 furthermore advantageously comprises means for automatically clearing the moving carriage 13 at the end of machining, consisting in raising the latter, particularly by rotating the output shaft 40 of the motor 12, in the opposite direction to the direction of machining, which, by virtue of the friction forces or of a mechanical antideflection device of the free wheel or viscous type (not depicted), causes the moving carriage 13 to tip away from the axis of rotation 18 of the abrasive disk 4, thus opening up access to the securing means 6 and 8 for the subsequent operations.

The wall 3 is advantageously made of an electrically insulating material so as to allow the detection of the presence of lubricating liquid in the machining compartment 31 by measuring the resistivity by applying a voltage between the bearing supports 20 and 21. This set-up also advantageously makes it possible to detect electrical contact between the moving carriage 13 and the bearing support 20 so as to inform the control electronics of the end of machining.

The machining compartment 31 is advantageously fitted with an articulated cover 70, as depicted in FIG. 2, allowing access to the interior of the compartment 31 and affording the environment outside the machine protection against splashes of lubricating liquid during the machining operation. The machine also advantageously comprises means (not depicted) for automatically opening the cover 70, these operating at the end of machining. Furthermore, the machine may comprise a system (not depicted) for automatically locking the cover 70, preventing inopportune opening therefore during machining.

The electronic command and control means consist of at least one electronic input/output board (not depicted) placed in the drive compartment 32. The inputs may, in particular, be connected to sensors as follows: a lubricating liquid level sensor, an end-of-machining sensor, a machining compartment lid open sensor, a cutting motor 5 current strength sensor and a temperature sensor. The outputs may be connected with the following commands: independent command of each motor, command of a visual interface for the user, command of the locking/unlocking of the cover 70.

One exemplary method of operation of the machine according to the invention will now be described, it being possible for this method of operation advantageously to be implemented by automatic control software in the context of automatic operation of the machine.

The following mode of operation is described chronologically from the state of the machine at the end of machining and for the next machining operation:

when the cover 70 is opened, the "open" sensor sends a signal to the command and control electronics; the latter responds by actuating the motor 11 which will move the motor 12 in translation, and therefore the shaft 16, and cause it to perform a series of low-amplitude back and forth movements so as to release the remains of blank resulting from an earlier machining operation from its residual bearing against the cutting disk 4, then will completely return the carriage against the wall 3;

at the same time, the motor 12 begins to run in the opposite direction to the direction for machining, driving the shaft 16 which itself, by virtue of the friction forces or a non-deflection device as explained earlier, causes the carriage to tip away from the axis 18 of the machining motor, toward the outside of the machine, to make the next operations easier;

the operator may separate by unscrewing the means 6, 8 for securing the blank and the template, as explained earlier; the template 9 is replaced by unsticking the old one and sticking in the new one L using the spike that forms part of the support 8 which will be bonded into a bore hole made in the template; the blank is replaced either by unsticking the old one, or by replacing its securing means 6 which may be one-use means; the template, its support, and a fresh blank support are assembled on the tubular element 50;

in order to optimize the amount of material to be machined, the operator offers up various centering jigs 60 to the template 9, and chooses the smallest one which can fit over the latter; the centering device is then folded down onto the carriage, pressed against the reference planes 64, 68, for example, and the corresponding blank 7 is coated with an adhesive that makes an instant bond, and slipped onto the housing 63 reserved for it on the centering jig 60, to be assembled by bonding with the blank-securing means 6;

the carriage 13 is folded down toward the inside of the machining compartment 31 and possibly moved, by virtue of push-buttons which advantageously command high-speed retreat and advance of the carriage, toward the desired machining start point; the protective cover is closed by the operator; the electronic control means check the water level, for example by analyzing the resistivity between the machining means and the movement means; the electronic control means check that the cover 70 has been closed, using a flexible blade switch placed, for example, in a stationary part of the casing 13 and a magnet placed in the cover which moves closer upon closure; if these two checks are passed, the machine is on standby and, by pressing either one of the two push-buttons described hereinabove, machining is begun;

the rotation motor 12 drives the rotation of the shaft 16 which, via the belt 17, drives the tubular element 50 and therefore the blank 7 and the template 9 in rotation, and the carriage 13 which is pressed toward the disk 4 and the feeler 10 by the internal friction forces; at the same time, the advance motor 11 starts, and, by virtue of the screw-nut system 14, 15, drives the translation of the motor 12, the shaft 16 and therefore the blank and the template, thus allowing systematic exploration of the exterior surface of the template by the feeler, except for the concave regions; at the same time, the cutting motor 5 starts up, driving the rotation of the abrasive disk 4; throughout the machining phase, the inputs of the electronic means check a certain number of sensors, including the closure of the cover, the water level, the internal temperature, the strength of the current drawn by the cutting motor 5, the manual push-buttons: if either one of the two push-buttons is depressed, it acts as an emergency stop; the end of machining by detection of electrical contact between the carriage 13 or the blank-securing means 6, on the one hand, and the bearing support 20 or the abrasive disk 4, or some other element of the machining assembly, on the other hand, the strength of the current drawn by the cutting motor 5 can control the speed of the motors 11 and 12 by virtue of an automatic control slaving means intended to optimize the machining rate to suit the machining forces;

when the advance movement of the carriage 13 is such that the template is no longer supported by the feeler, the carriage drops towards the bearing support 20 of the machining subassembly, electrical contact is made and the three motors 5, 11, 12 stop; the machined part is cut off from the rest of the blanks, and drops into the bottom of the machining compartment 31; if droppage were not to take place, machining would continue until the blank had been machined away and the blank-securing means would reach the abrasive disk, itself also metal, and the end-of-machining contact would then cause the three motors to stop; the cycle is finished, and returns to its start when the cover is opened; when the cover is open, it can be removed by extracting its spindle, allowing easy emptying and cleaning of the machining compartment 31.

What is claimed is:

1. A machine for machining at least one volume of work piece automatically by copying, comprising:

a machining tool with an axis of symmetry and having at least one degree of freedom in rotation about the axis of symmetry, means for driving the rotation of said machining tool about its axis of symmetry, means for securing a blank, in which said volume is machined, having at least one degree of freedom in rotation, means for driving the rotation of said blank-securing means, means for securing a template, having at least one degree of freedom in rotation, means for driving the rotation of said template-securing means, a feeler capable of coming into contact with the exterior surface of said template, means for bringing about relative movement between said blank-securing means and said machining tool, and between said template-securing means and said feeler, said movement means allowing the machining tool and the feeler to remain in constant contact with, respectively, said blank and said template, means for commanding and controlling said means for driving the rotation of the machining tool, said means for driving rotation of the template-securing means and said movement means, wherein said machining tool comprises an abrasive disk and said movement means comprise a moving carriage on which said blank-securing means and said template-securing means are mounted so that they are free to rotate, said moving carriage having at least two degrees of freedom of movement.

2. The machine as claimed in claim 1, wherein said two degrees of freedom of said moving carriage are one degree of freedom in rotation and one degree of freedom in translation, and in that said movement means comprise means for driving the translation and means for driving the rotation of said moving carriage.

3. The machine as claimed in claim 2, further comprising a rigid support and wherein said means for driving the translation of said moving carriage comprise a first motor connected completely to said rigid support, said means for driving the rotation of said blank-securing means and said means for securing the template comprise a second motor connected to said first motor via a screw-nut connection, and wherein said moving carriage is free in rotation about the output shaft of said second motor, said output shaft being guided in rotation and in translation by said rigid support.

4. The machine as claimed in claim 3, wherein said means for driving the rotation of said moving carriage about the output shaft of said second motor comprise the friction forces generated by the rotation said blank-securing means and of said means for securing the template.

5. The machine as claimed in claim 4, wherein said blank-securing means and said means for securing the template are connected completely and have aligned axes of rotation.

6. The machine as claimed in claim 5, wherein the axis of rotation of said abrasive disk is parallel to the axes of rotation of said blank-securing means and of said means for securing the template, said rigid support having a flat wall perpendicular to said axis of rotation of the abrasive disk separating a machining compartment from a drive compartment.

7. The machine as claimed in claim 6, wherein the axis of rotation of said abrasive disk and the output shaft of said second motor are mounted in identical respective bearing supports.

8. The machine as claimed in any one of claims 1 to 7, wherein said feeler is secured rigidly to said rigid support so as, by its abrasion resulting from the rubbing against the template, to compensate for the wear of said abrasive disk.

9. The machine as claimed in any of claims 1 to 7, further comprising means for moving said feeler radially, so as to establish a given dimensional ratio at which the inlay is reproduced with respect to the template, in a plane perpendicular to an axis of rotation of said template.

10. The machine as claimed in claim 1, wherein said feeler has a thickness greater than the thickness of said abrasive disk so as to increase the longitudinal dimension of the inlay with respect to that of said template.

11. The machine as claimed in claim 1, wherein said blank-securing means and said, means for securing the template are connected by a screw-nut connection, said blank-securing means being secured rigidly to one of said elements—screw or nut—and said template-securing means being secured rigidly to the, complementary other one of said elements—nut or screw.

12. The machine as claimed in claim 1, further comprising means for automatically stopping operation at the end of machining by detecting that said moving carriage is in a given position.

13. The machine as claimed in claim 1, further comprising a disk which is abrasive over all or part of its two opposite faces, said two opposite faces converging toward the periphery of the disk.

14. The machine as claimed in claim 1, further comprising means for slaving said movement means to the force exerted by the abrasive disk on the blank.

15. The machine as claimed in claim 1, further comprising means for lubricating said machining disk by splash lubrication.

16. The machine as claimed in claim 1, further comprising means for reversing the direction of rotation of said abrasive disk.

17. The machine as claimed in claim 1, further comprising means for automatically clearing said moving carriage at the end of machining.

18. The machine as claimed in claim 1, further comprising a centering jig allowing the blank to be secured to said blank-securing means, and allowing the template to be secured to said template-securing means in such a way that the inlay to be obtained lies within the volume of the blank.

19. The machine as claimed in claim 1, wherein said blank and said template are secured to their respective securing means via at least one of their respective ends.

* * * * *